FIRE-RESISTANT CONSTRUCTION MATERIAL

This is a continuation of application Ser. No. 613,476 filed Sept. 15, 1975, and now abandoned.

BACKGROUND OF THE INVENTION

Numbers of fire-resistant construction materials are known and in common use. These construction materials are normally available in panel, preferably rigid panel, form so as to be useful as, or as a substantial portion of, common building parts.

These construction materials are relied upon to impart fire-resistance or fire-proofing in buildings and commonly replace, or partially replace, wood and similar flammable construction materials. Thus, for example, fire-resistant construction materials may be provided in panel form so as to constitute the structural facing of walls, ceilings, doors and the like.

It is also known to face these fire-resistant construction materials with a laminate, paint, or other cosmetic coating which may itself be either flammable or inflammable. In instances where a flammable facing or coating is applied to these fire-resistant construction materials, the construction materials serves as a fire-resistant barrier which provides insulation or separation of flammable building materials and thus also serves as a means of avoiding spread of flames in the event of fire.

A common example of the use of fire-resistant construction materials as a portion of a building material is in the core of a door. Such a construction is exemplified by U.S. Pat. No. 3,196,494 of Hartman et al, the disclosure of which is incorporated herein by reference. In such a door, the fire-resistant construction material constitutes its main structural support. The construction material itself need not be apparent, however, as it may be covered with, for example, a thin veneer of wood to give the appearance that the door is solid wood. Unlike solid wood, however, the door will not burn and will serve as a barrier for any fire which might occur on one side or the other.

One of the most common fire-resistant construction materials now in use comprises panels of a mixture of cement and asbestos. In such materials, the cement acts largely as an inert binder for the incombustible component, asbestos. Such construction materials, however, have serious disadvantages in use. They are extremely brittle and require special care in handling. Also, they cannot be nailed directly due to their poor impact strength. Accordingly, pre-drilling of holes is a necessity. Moreover, special tools must ordinarily be used to cut the panels and special molding, where they are mounted or otherwise fixed in position.

In Canadian Pat. No. 897,855 of Hartman, there is disclosed an improvement to the cement binder fire-resistant construction materials. That Canadian Patent describes structures in which incombustible components are dispersed and fixed into rigid panels with a two-part binder consisting of phenol formaldehyde resin and urea formaldehyde resin. Significantly, that invention overcomes many of the problems of special handling, brittleness, and low impact strength of fire-resistant construction materials containing cement.

Even the two-part binder system of this Canadian patent has not, however, met with complete success. In particular, the preparation of rigid panels from the fire-resistant construction material there described must be performed within a short period of time because of the limited pot life of the resin composition. Further, because water is required for the formation of such construction materials, difficulties with surface migration of salts such as certain incombustible components in the material have been encountered during the curing of the resin into a fixed panel. This migration may lead to an eventually heterogeneous composition and, by virtue of the surface location of such salts, may result in a panel in which important incombustible components may be only lightly bound and therefore are susceptible to loss through abrasion.

INTRODUCTION TO THE INVENTION

It is an object of this invention to provide fire-resistant construction material in the form of rigid panels of improved physical properties which may be handled as if they were made of wood.

It is a further object of this invention to provide fire-resistant construction materials comprising an incombustible component intimately dispersed and fixed into a rigid panel by an organic resin binder which can be produced from a stable dry particulate powder. It is desired that the admixture powder, once prepared, may be formed into a rigid panel whenever desired and without concern of premature setting.

Still another object of this invention is a stable, articulate powder which may be formed into a rigid panel of fire-resistant construction material in the absence of water so as to eliminate the migration of powder constituents during curing and ensure the homogeneity of the resultant panel.

These objects, and further advantages as are described herein, are obtained by the present invention.

DESCRIPTION OF THE INVENTION

This invention revolves about the use of melamine formaldehyde resin as a binder in fire-resistant construction material. More particularly, it has been discovered that melamine formaldehyde resin may be admixed with a particulate, incombustible component for fire-resistant construction materials and that this blend of intimately dispersed powder may then be fixed into a rigid panel by curing the resin.

The cured and resin-bound panels of this fire-resistant construction material exhibit unusually desirable properties. They may be handled in much the same manner as ordinary lumber. Thus, for example, they may be directly nailed, drilled, painted, laminated and otherwise treated in the same manner as if they were a wood construction material. In contrast to these woody materials, however, the present resin-bound panels exhibit fire-resistance and, if desired, improved intumescent properties so as to provide substantial protection in the event of fire.

The present fire-resistant construction materials may be formed by curing a powdered blend of the dry melamine formaldehyde resin with suitable incombustible components as are known in the art for their properties of fire-resistance. Curing of the melamine formaldehyde resin—which step fixes the powdered precursor of the present construction material into a rigid panel—may be simply performed. All that is necessary is that sufficient pressure and temperature be applied to the blend to transform it into a rigid, continuously adherent network.

Suitable conditions for curing of the resin-containing blend are temperatures of at least about 250° F., preferably from about 300° to 400° F., and pressures of at least

DIPEPTIDE DERIVATIVES

BACKGROUND OF THE INVENTION

The use of N-acetyl-L-alanyl-L-prolyl-isopropylamide as an elastase inhibitor is disclosed in Biochem. 13, 5495 (1974).

DESCRIPTION OF THE INVENTION

The dipeptide derivatives provided by the present invention have the following general formula

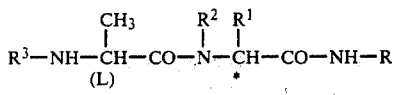

wherein R represents a methyl, ethyl, propyl or isopropyl group; $R^1$ and $R^2$ each represent a hydrogen atom or a methyl group, with the proviso that $R^1$ and $R^2$ do not simultaneously represent a hydrogen atom, or $R^1$ and $R^2$ together represent a trimethylene group; $R^3$ represents an acyl group derived from a carboxylic acid, a sulphonic acid or a sulphinic acid with the proviso that when the acyl group is derived from an unsubstituted alkanoic acid said acid contains at least three carbon atoms; and the asterisk denotes that the configuration at the carbon atom so-marked is L when $R^1$ represents other than a hydrogen atom.

The acyl group denoted by $R^3$ in formula I can represent, for example, an unsubstituted alkanoyl group containing at least three carbon atoms or a halo-alkanoyl, nitro-alkanoyl, cyano-alkanoyl, cycloalkylcarbonyl, cycloalkyl-alkanoyl, aroyl, aryl-alkanoyl, alkoxycarbonyl, aryloxycarbonyl, aryl-alkoxycarbonyl, arylsulphonyl, alkylsulphonyl, cycloalkylsulphonyl, cycloalkylsulphinyl, cycloalkyl-alkylsulphonyl or cycloalkyl-alkylsulphinyl group.

As used in this specification, the term "alkanoyl" means an alkanoyl group derived from a straight-chain or branched-chain alkanoic acid, preferably a lower alkanoyl group such as acetyl, propionyl, butyryl, isobutyryl, valeroyl, pivaloyl etc, subject to the proviso that when $R^3$ represents an unsubstituted alkanoyl group said group contains at least three carbon atoms. The term "halo-alkanoyl" means an alkanoyl group which carries one or more halogen atoms. The halo-alkanoyl group is preferably a halo-(lower alkanoyl) group such as monochloroacetyl, dichloroacetyl or, especially, trifluoroacetyl. The term "nitro-alkanoyl" means an alkanoyl group carrying a nitro group, preferably a nitro-(lower alkanoyl) group such as nitroacetyl. The term "cyano-alkanoyl" means an alkanoyl group carrying a cyano group, preferably a cyano-(lower alkanoyl) group such as cyanoacetyl. The term "cycloalkylcarbonyl" means a group of the formula $R^6$—CO— in which $R^6$ represents a lower cycloalkyl group (i.e. a monocyclic cycloalkyl group which contains from 3 to 8 carbon atoms such as cyclopentyl and cyclohexyl) or an aliphatic bridged and/or condensed ring system which may be substituted by oxo or hydroxy. An example of a cycloalkylcarbonyl group containing such a ring system is adamantylcarbonyl. The term "cycloalkyl-alkanoyl" means an alkanoyl group in which one of the hydrogen atoms has been replaced by the group $R^6$ hereinbefore (e.g. adamantylacetyl). The term "aroyl" means an aroyl group (e.g. benzoyl) which may carry one or more substituents selected from halogen, lower alkyl, lower alkoxy, nitro, amino, lower alkanoylamino etc. The term "aryl-alkanoyl" means an alkanoyl group in which one of the hydrogen atoms has been replaced by an aryl group, the term "aryl" meaning an aryl group (e.g. phenyl) carrying one or more substituents selected from halogen, lower alkyl, lower alkoxy, nitro, amino, lower alkanoylamino etc. The preferred aryl-alkanoyl groups are the aryl-(lower alkanoyl) groups such as the phenacetyl, phenylpropionyl and like groups. The term "alkoxycarbonyl" means a straight-chain or branched-chain alkoxycarbonyl group, preferably a lower alkoxycarbonyl group such as methoxycarbonyl, ethoxycarbonyl etc. The term "aryloxycarbonyl" means an aryloxycarbonyl group in which the aryl group is as defined earlier. The term "aryl-alkoxycarbonyl" means an alkoxycarbonyl group in which one of the hydrogen atoms has been replaced by an aryl group as defined earlier, preferably an aryl-(lower alkoxycarbonyl) group such as the benzyloxycarbonyl group. The term "arylsulphonyl" means an arylsulphonyl group in which the aryl group is as defined earlier. For example, the arylsulphonyl group may be the benzenesulphonyl group or a naphthalenesulphonyl group (e.g. 1-naphthalenesulphonyl) or a benzenesulphonyl group carrying one or more substituents which may be present on the aforementioned aryl group (e.g. p-toluenesulphonyl, 4-chlorobenzenesulphonyl, 4-aminobenzenesulphonyl, 4-acetylaminobenzenesulphonyl, 4-methoxybenzenesulphonyl, mesitylenesulphonyl etc). The alkylsulphonyl group is preferably a lower alkylsulphonyl group such as methylsulphonyl etc. The term "cycloalkylsulphonyl" means a group of the formula $R^6$—$SO_2$— in which $R^6$ has the significance given earlier, examples of such groups being adamantylsulphonyl (e.g. 1-adamantylsulphonyl), camphorsulphonyl (e.g. D-10-camphorsulphonyl) etc. The term "cycloalkylsulphinyl" means a group of the formula $R^6$—SO— in which $R^6$ has the significance given earlier, examples of such groups being adamantylsulphinyl such as 1-adamantylsulphinyl. The term "cycloalkyl-alkylsulphonyl" means an alkylsulphonyl group which carries a substituent $R^6$ hereinbefore (e.g. isobornylmethylsulphonyl etc) and the term "cycloalkyl-alkylsulphinyl" means an alkylsulphinyl group which carries a substituent $R^6$ hereinbefore (e.g. bornylmethylsulphinyl etc). The terms "lower alkanoyl", "lower alkyl" and "lower alkoxy" as used herein, alone or in combination as the context may require, mean that such groups preferably contain up to 6 carbon atoms. Examples of lower alkyl and lower alkoxy groups which, like the lower alkanoyl groups, can be straight-chain or branched-chain, are methyl, ethyl, propyl, isopropyl etc, and methoxy, ethoxy, propoxy, isopropoxy etc, respectively.

In one particular embodiment of the present invention, $R^3$ represents an unsubstituted lower alkanoyl group containing at least three carbon atoms or a lower cycloalkylcarbonyl, benzoyl, phenyl-(lower alkanoyl), lower alkoxycarbonyl, phenoxycarbonyl, phenyl-(lower alkoxycarbonyl), benzenesulphonyl, naphthalenesulphonyl or lower alkylsulphonyl group, the benzoyl, phenoxycarbonyl and benzenesulphonyl groups and the phenyl portion of the phenyl-(lower alkanoyl) and phenyl-(lower alkoxycarbonyl) groups optionally carrying one or more substituents selected from halogen, lower alkyl, lower alkoxy and nitro.

of an inert organic solvent such as dimethylformamide or ethyl acetate at a low temperature.

Yet again, for example, an amide of formula II can be condensed with an N-protected-L-alanine in which the carboxyl group is in the form of an active ester group (e.g. the p-nitrophenyl, 2,4,5-trichlorophenyl, N-hydroxysuccinimide or hydroxybenztriazole ester group). This condensation is suitably carried out in an inert organic solvent such as dimethylformamide, tetrahydrofuran etc.

Further, for example, an amide of formula II can be condensed with an N-protected-L-alanine in the presence of dicyclohexylcarbodiimide. This condensation is expediently carried out in the presence of an inert organic solvent (e.g. dimethylformamide or methylene chloride) at a low temperature (e.g. 0° C.).

Still further, for example, an amide of formula II can be condensed with an N-protected-L-alanine in which the carboxyl group is in the form of an acid chloride. It is preferred to carry out this condensation in the presence of a base (e.g. an alkali metal hydroxide such as sodium hydroxide) and at a low temperature (e.g. 0° C.).

The amidation of a starting material of formula IV in accordance with embodiment (b) of the present process can be carried out according to methods known per se. Thus, for example, a compound of formula IV in which $R^2$ represents a methyl group or $R^1$ and $R^2$ together represent a trimethylene group can be converted in the manner described earlier in connection with the condensation of an amide of formula II with an N-protected-L-alanine of formula III into an acid azide, activated ester, mixed anhydride or acid chloride as the case may require and can then be reacted with an appropriate amine yielding the group denoted by R hereinbefore. Alternatively, a carboxylic acid of formula IV in which $R^2$ represents a methyl group or $R^1$ and $R^2$ together represent a trimethylene group can be amidated in the presence of dicyclohexylcarbodiimide. In the amidation of a compound of formula IV in which $R^2$ represents a hydrogen atom, care must be taken that no racemisation occurs. This latter amidation can suitably be carried out according to the acid azide or N-hydroxysuccinimide dicyclohexylcarbodiimide method, in each case depending on the nature of $R^5$ in the compound of formula IV. Another amidation method comprises treating an appropriate ester of formula IV (e.g. a methyl ester) with an amine yielding the group R hereinbefore.

The condensation of an amide of formula II with an N-protected-L-alanine of formula III or the amidation of a starting material of formula IV yields a compound of the general formula

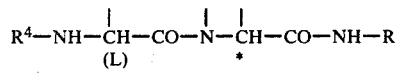

(V)

wherein R, $R^1$, $R^2$, $R^4$ and the asterisk have the significance given earlier.

It will be appreciated that compounds of formula V in which the protecting group denoted by $R^4$ is the trifluoroacetyl or p-toluenesulphonyl group or a lower alkoxycarbonyl, aryloxycarbonyl or aryl-(lower alkoxycarbonyl) group correspond to dipeptide derivatives of formula I in which $R^3$ has any of these values.

The protecting group denoted by $R^4$ can be cleaved off from a compound of formula V according to known methods. For example, the cleavage of the trifluoroacetyl group can be carried out by treatment with an appropriate base (e.g. an alkali metal hydroxide such as sodium hydroxide). The cleavage of the p-toluenesulphonyl group can be carried out by treatment with an alkali metal (e.g. sodium) in liquid ammonia. The cleavage of a lower alkoxycarbonyl, aryloxycarbonyl, aryl-(lower alkoxycarbonyl) group or the 2-(biphenylyl)-isopropyloxycarbonyl group can be carried out by hydrolysis (e.g. by treatment with hydrogen bromide in glacial acetic acid). An aryl-(lower alkoxycarbonyl) group can also be cleaved off by hydrogenolysis (e.g. in the presence of palladium-on-charcoal or platinum oxide). The tert.butoxycarbonyl or 2-(biphenylyl)-isopropyloxycarbonyl group may also be cleaved off using hydrogen chloride in dioxan or trifluoroacetic acid.

The cleavage of the protecting group denoted by $R^4$ from a compound of formula V yields a compound of the general formula

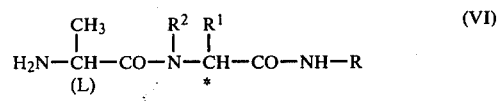

(VI)

, wherein R, $R^1$, $R^2$ and the asterisk have the significance given earlier,
which may be isolated if desired, suitably in the form of a hydrohalide salt such as the hydrobromide, and then converted into a dipeptide derivative of formula I by the introduction of the group $R^3$ according to methods known per se or which may be converted in situ into a dipeptide derivative of formula I in the same manner.

The introduction of a group denoted by $R^3$ into a compound of formula VI is carried out in accordance with methods which are known per se.

Thus, for example, in one method, a compound of formula VI can be treated with an appropriate acid chloride (e.g. an alkanoic acid chloride such as pivaloyl chloride, a cycloalkane carboxylic acid chloride such as cyclohexane carboxylic acid chloride, an aroic acid chloride such as benzoyl chloride, an arylalkanoic acid chloride such as phenacetyl chloride, an arylsulphonic acid chloride such as p-toluenesulphonyl chloride or an alkanesulphonyl chloride such as methanesulphonyl chloride in the presence of a base (e.g. an alkali metal hydroxide such as sodium hydroxide or a tertiary amine such as triethylamine or pyridine). This treatment is advantageously carried out at about room temperature. It is advantageous to carry out this treatment in the presence of an inert organic solvent such as a halogenated hydrocarbon (e.g. methylene chloride) when an alkali metal hydroxide is used as the base. When a tertiary amine is used as the base, it can be present in excess and can thereby also serve as a solvent.

In another method, for example, a compound of formula VI can be treated with an appropriate acid anhydride (e.g. a lower alkanoic acid anhydride such as propionic anhydride, isobutyric anhydride or n-valeric anhydride) in the presence of a base, preferably a tertiary amine and, in particular, pyridine. It is expedient to carry out this treatment at about room temperature. An excess of the tertiary amine can be present and can thereby also serve as a solvent. This treatment can, however, also be carried out in the presence of an appropriate inert organic solvent.

In a further method, for example, a compound of formula VI can be treated with an appropriate chloroformate in the presence of N-ethylmorpholine. Examples of chloroformates which may be used in this method are the lower alkyl chloroformates, particularly ethyl chloroformate and isobutyl chloroformate. This treatment may be carried out in an inert organic solvent (e.g. tetrahydrofuran) and at a temperature of about room temperature.

In yet a further method, a hydrohalide salt, particularly the hydrobromide salt, of a compound of formula VI can be condensed with an appropriate acid yielding the group denoted by $R^3$ in the presence of a suitable condensing agent such as a carbodiimide (e.g. N,N-dicyclohexylcarbodiimide) in accordance with known procedures. The condensation is carried out in the presence of a tertiary amine (e.g. triethylamine or N-ethylmorpholine) and preferably in the presence of an inert organic solvent such as a chlorinated hydrocarbon (e.g. methylene chloride). It is expedient to carry out the condensation at about 0° C.

The oxidation of a dipeptide derivative of formula I in which $R^3$ represents an acyl group derived from a sulphinic acid to give a corresponding dipeptide derivative of formula I in which $R^3$ represents an acyl group derived from a sulphonic acid can be carried out in accordance with methods known per se. Suitable oxidising agents which can be used include potassium permanganate in acetone and organic peracids such as peracetic acid, perbenzoic acid etc. The organic peracid may be formed in situ using hydrogen peroxide and the corresponding organic acid (e.g. hydrogen peroxide and glacial acetic acid). The oxidation is expediently carried out at about room temperature, but in certain circumstances it can be advantageous to warm the oxidation mixture (e.g. up to about 65° C.).

The amide starting materials of formula II can be prepared, for example, by amidating a corresponding N-protected α-amino carboxylic acid in a manner analogous to that described earlier in connection with the amidation of a carboxylic acid of formula IV and subsequently removing the N-protecting group in a manner analogous to that described earlier in connection with the cleavage of the protecting group $R^4$ from a compound of formula VI.

The N-protected-L-alanine starting materials of formula III are known compounds which can be prepared according to conventional methods from L-alanine.

The starting materials of formula IV can be prepared, for example, by condensing an N-protected-L-alanine with a lower alkyl or aryl-(lower alkyl) ester of L-alanine, L-proline, N-methyl-L-alanine or sarcosine in accordance with methods known per se (e.g. the mixed anhydride, azide, activated ester or acid chloride method described earlier in connection with the condensation of an amide of formula II with an N-protected-L-alanine of formula III) and, if desired, hydrolysing a resulting ester to the corresponding carboxylic acid.

The dipeptide derivatives of formula I hereinbefore possess activity as elastase inhibitors.

Thus, for example, the present dipeptide derivatives in which $R^3$ represents an unsubstituted alkanoyl group containing at least 3 carbon atoms or a halo-alkanoyl, nitro-alkanoyl, cyano-alkanoyl, lower cycloalkylcarbonyl, lower cycloalkyl-alkanoyl, aroyl, aryl-alkanoyl, alkoxycarbonyl, aryloxycarbonyl or aryl-alkoxycarbonyl group possess an in vitro elastase inhibiting activity against porcine pancreatic elastase. This activity can be demonstrated according to the test method of Visser L. and Blout E. R., Biochem. Biophys. Acta 268 (1972) 257, using porcine pancreatic elastase as the enzyme.

The results obtained with representative dipeptide derivatives in this test are given in Table I hereinafter, the $K_i$ being the inhibitor constant in millimoles per liter:

Table I

| Dipeptide derivative | $K_i$ (mmol/liter) |
|---|---|
| N-Benzoyl-L-alanyl-L-proline ethylamide | 0.026 |
| N-Pivaloyl-L-alanyl-L-proline ethylamide | 0.09 |
| N-(n-Valeryl)-L-alanyl-L-proline ethylamide | 0.08 |
| N-Isobutanoyl-L-alanyl-L-proline ethylamide | 0.06 |
| N-Cyclohexanoyl-L-alanyl-L-proline ethylamide | 0.01 |
| N-Phenacetyl-L-alanyl-L-proline ethylamide | 0.086 |
| N-Benzoyl-L-alanyl-L-alanine ethylamide | 0.12 |

Again, for example, the present dipeptide derivatives in which $R^3$ represents a cycloalkylcarbonyl or cycloalkyl-alkanoyl group, in which the cycloalkyl moiety is an aliphatic bridged and/or condensed ring system which may be substituted by oxo or hydroxy, or an arylsulphonyl, alkylsulphonyl, cycloalkylsulphonyl, cycloalkylsulphinyl, cycloalkyl-alkylsulphonyl or cycloalkyl-alkylsulphinyl group possess an in vitro elastase inhibiting activity against human granulocyte elastase. This activity can be demonstrated according to the aforementioned test method using human granulocyte elastase as the enzyme. The result obtained with a representative dipeptide derivative in this test is given in Table II hereinafter, the $I_{50}$ being the concentration in millimoles per liter which gives 50% inhibition of the human granulocyte elastase:

Table II

| Dipeptide derivative | $I_{50}$ |
|---|---|
| N-(p-Toluenesulphonyl)-L-alanyl-L-proline ethylamide | 0.9 |

The in vivo elastase inhibiting activity of the present dipeptide derivatives in which $R^3$ represents an unsubstituted lower alkanoyl group containing at least 3 carbon atoms or a lower cycloalkanoyl, aroyl, aryl-(lower alkanoyl), lower alkoxycarbonyl, aryloxycarbonyl or aryl-(lower alkoxycarbonyl) group can be demonstrated, for example, by administering them orally or intraperitoneally to rats in which an oedema has previously been induced in a hind paw by the subcutaneous injection therein of a proteolytic enzyme such as porcine pancreatic elastase. Following such oral or parenteral administration of such dipeptide derivatives the size of the oedema is reduced.

The dipeptide derivatives of formula I hereinbefore may be used in the treatment of degenerative diseases associated with the action of elastase-like enzymes such as emphysema and arthritis. They may also be used for the treatment of inflammatory conditions in which elastase-like enzymes act as mediators of inflammation. Further, they may be used as adjuncts to topical antifungal and antibacterial preparations for the treatment of infections associated with the breakdown of host-elastic tissue.

The dipeptide derivatives of formula I hereinbefore may be used as medicaments in the form of pharmaceutical preparations which contain them in association with a compatible pharmaceutical carrier material. This carrier material may be an organic or inorganic inert carrier material suitable for enteral (e.g. oral) or parenteral administration. Examples of such carrier materials include water, lactose, starch, magnesium stearate, talc, gum arabic, gelatin, polyalkyleneglycols, petroleum jelly etc. The pharmaceutical preparations can be made up in a solid form (e.g. as tablets, dragees, suppositories or capsules) or in a liquid form (e.g. as solutions, emulsions, suspensions or aerosols). The pharmaceutical preparations may be subjected to customary pharmaceutical operations such as sterilisation and may contain adjuvants such as preserving agents, stabilising agents, wetting agents, salts for varying the osmotic pressure etc.

The dipeptide derivatives provided by the present invention can be expediently administered in a dosage range of from about 5 mg to 30 mg, preferably 10 mg, per day. It will, of course, be appreciated that this dosage range is given by way of example only and that it can be varied upwards or downwards depending on factors such as the particular dipeptide derivative to be administered, the particular condition to be treated and the individual requirements of the patient as determined by the attending physician.

The following Examples illustrate the process provided by the present invention:

EXAMPLE 1

(A) The preparation of the starting material (i) N-Benzyloxycarbonyl-L-alanine ethylamide 33.48 g (0.15 mol) of N-benzyloxycarbonyl-L-alanine were dissolved in 225 ml of dry tetrahydrofuran and the solution was cooled to $-10°$ C. 22.95 ml (0.15 mol) of triethylamine and 19.8 ml (0.15 mol) of isobutyl chloroformate were then added and the solution was stirred at $-10°$ C. for 20 minutes. To this mixture was then added a solution of 7.53 g (0.15 mol) of monoethylamine in 215 ml of dimethylformamide. The solution was stirred at $-10°$ C. for 5 minutes and then left to stand for 16 hours at room temperature. The solvents were removed by evaporation and the residue was triturated with 450 ml of ethyl acetate and washed successively with 200 ml of 1-N hydrochloric acid, 200 ml of water and 200 ml of 5% sodium bicarbonate solution. After drying over sodium sulphate and filtration, the solvent was removed by evaporation. The resulting oil crystallised on the addition of petrol to yield 22.70 g (60.5%) of N-benzyloxycarbonyl-L-alanine ethylamide of melting point 127°–128° C.; $[\alpha]_D^{20} = +11.2°$ (c=0.83% in dimethylformamide).

(ii) L-Alanine ethylamide hydrobromide 10 g (0.04 mol) of N-benzyloxycarbonyl-L-alanine ethylamide were stirred for 1 hour in 50 ml of 4-N hydrobromic acid in acetic acid. To the solution were added 300 ml of dry ether and, after stirring for a few minutes, the white solid was allowed to settle and the ether decanted from the solid. The yield of L-alanine ethylamide hydrobromide obtained was 8.0 g (96.6%).

(B) The process (i) N-Benzyloxycarbonyl-L-alanyl-L-alanine ethylamide 7.5 g (0.034 mol) of N-benzyloxycarbonyl-L-alanine were dissolved in 50 ml of dry tetrahydrofuran and the solution was cooled to $-5°$ C. 4.26 ml (0.034 mol) of N-ethylmorpholine and 4.14 ml (0.034 mol) of pivaloyl chloride were then added and the solution was stirred at $-5°$ C. for 30 minutes. To this mixture was then added a solution of 7.0 g (0.034 mol) of L-alanine ethylamide hydrobromide in 50 ml of dimethylformamide followed by 8.5 ml (0.068 mol) of N-ethylmorpholine. The solution was stirred at $-10°$ C. for 1 hour and then left to stand for 16 hours at room temperature. The solvents were removed by evaporation; the product crystallising on the addition of water. The yield of N-benzyloxycarbonyl-L-alanyl-L-alanine obtained was 9.05 g (83%); melting point 203°–205° C.; $[\alpha]_D^{20} = -1.1°$ (c=1.02% in dimethylformamide; $[\alpha]_{365}^{20} = -9.2°$ (c=1.02% in dimethylformamide).

(ii) L-Alanyl-L-alanine ethylamide hydrobromide 7.5 g (0.023 mol) of N-benzyloxycarbonyl-L-alanyl-L-alanine ethylamide were stirred for 1 hour in 50 ml of 4-N hydrobromic acid in acetic acid. To the solution were added 300 ml of dry ether and, after stirring for a few minutes, the oil was allowed to settle and the ether decanted from the oil and discarded. The oil was then dissolved in methanol, the desired L-alanyl-L-alanine ethylamide hydrobromide crystallising out on the addition of ethyl acetate. The yield was 6.0 g (83%) and the melting point was 229°–231° C.; $[\alpha]_D^{20} = -28.0°$ (c=1% in water).

(iii) N-Propionyl-L-alanyl-L-alanine ethylamide 1.75 g (0.0065 mol) of L-alanyl-L-alanine ethylamide hydrobromide were dissolved in 40 ml of pyridine and 4.2 ml (0.013 mol) of propionic anhydride were added. The solution was stirred for 1 hour at room temperature and then the pyridine was removed by evaporation. The resulting solid was recrystallised from ethanol. The yield of N-propionyl-L-alanyl-L-alanine ethylamide obtained was 1.15 g (72.5%); melting point 289°–291° C.; $[\alpha]_D^{20} = -76.7°$ (c=0.95% in methanol).

Analysis for $C_{11}H_{21}O_3N_3$ (243.31) Calculated: C: 54.30; H: 8.70; N: 17.27. Found: C: 54.11; N: 8.74; N: 17.28.

(iv) N-Benzoyl-L-alanyl-L-alanine ethylamide 2.35 g (0.0087 mol) of L-alanyl-L-alanine ethylamide hydrobromide were suspended in 40 ml of pyridine and 2.04 ml (0.02 mol) of benzoyl chloride were added. The mixture was then stirred for 2 hours at room temperature. The solvent was evaporated and the residue recrystallised from isopropanol to yield 1.3 g (51%) of N-benzoyl-L-alanyl-L-alanine ethylamide of melting point 237°–239° C; $[\alpha]_D^{20} = -17.8°$ (c=1.01% in methanol).

Analysis for $C_{15}H_{21}O_3N_3$ (291.35) Calculated: C: 61.84; H: 7.26; N: 14.42. Found: C: 61.86; H: 7.39; N: 14.42.

(v) N-Pivaloyl-L-alanyl-L-alanine ethylamide

In a similar manner to that described in part (iv) earlier there was prepared N-pivaloyl-L-alanyl-L-alanine ethylamide in a yield of 59% (recrystallised from ethanol); melting point 238°–241° C.; $[\alpha]_D^{20} = -4.2°$ (c=1.22% in dimethylformamide).

Analysis for $C_{13}H_{25}O_3N_3$ (271.36) Calculated: C: 57.54; H: 9.29; N: 15.48. Found: C: 57.32; H: 9.12; N: 15.26.

EXAMPLE 2

(A) The Preparation of the Starting Material (i) N-Benzyloxycarbonyl-L-alanine isopropylamide In a similar manner to that described in Example 1(A)(i) there was obtained N-benzyloxycarbonyl-L-alanine isopropylamide in a yield of 82% (crystallised under petrol); melting point 153°–156° C.

Analysis for $C_{14}H_{20}O_3N_2$ (264.33) Calculated: C: 63.62; H: 7.63; N: 10.59. Found: C: 62.93; H: 7.73; N: 10.30; $H_2O$: 1.17%.

Water-free: C: 63.67; H: 7.69; N: 10.42.

(ii) L-Alanine isopropylamide hydrobromide

This compound was prepared from N-benzyloxycarbonyl-L-alanine isopropylamide in a manner analogous to that described in Example 1(A) (ii).

(B) The Process

(i) N-Benzyloxycarbonyl-L-alanyl-L-alanine isopropylamide

In a similar manner to that described in Example 1(B) (i), from N-benzyloxycarbonyl-L-alanine and L-alanine isopropylamine hydrobromide there was obtained N-benzyloxycarbonyl-L-alanyl-L-alanine isopropylamine in a yield of 65% (recrystallised from ethanol); melting point 233°–235° C.

(ii) L-Alanyl-L-alanine isopropylamide hydrobromide

In a similar manner to that described in Example 1(B) (ii), from N-benzyloxycarbonyl-L-alanyl-L-alanine isopropylamide there was obtained L-alanyl-L-alanine isopropylamide hydrobromide.

(iii) N-Propionyl-L-alanyl-L-alanine isopropylamide

In a similar manner to that described in Example 1(B) (iii) from L-alanyl-L-alanine isopropylamide hydrobromide and propionic anhydride there was obtained N-propionyl-L-alanyl-L-alanine isopropylamide in a yield of 82% (recrystallised twice from methanol); melting point 290°–292° C.; $[\alpha]_D^{20} = -83.4°$ (c=1.02% in acetic acid).

Analysis for $C_{12}H_{23}O_3N_3$ (257.34) Calculated: C: 56.01; H: 9.01; N: 16.23. Found: C: 56.08; H: 8.84; N: 16.15.

EXAMPLE 3

(A) The Preparation of the Starting Material

(i) N-Benzyloxycarbonyl-sarcosine ethylamide

In a similar manner to that described in Example 1(A) (i), there was obtained N-benzyloxycarbonyl-sarcosine ethylamide in a yield of 51% (recrystallised from ethyl acetate/petrol); melting point 69°–71° C.

Analysis for $C_{13}H_{18}O_3N_2$ (250.30) Calculated: C: 62.38; H: 7.25; N: 11.19. Found: C: 62.54; H: 7.40; N: 11.27.

(ii) Sarcosine ethylamide hydrobromide

In a similar manner to that described in Example 1(A) (ii), from N-benzyloxycarbonyl-sarcosine ethylamide there was obtained sarcosine ethylamide hydrobromide.

(B) The Process

(i) N-Benzyloxycarbonyl-L-alanyl-sarcosine ethylamide

In a similar manner to that described in Example 1(B) (i), from N-benzyloxycarbonyl-L-alanine and sarcosine ethylamide hydrobromide there was obtained N-benzyloxycarbonyl-L-alanyl-sarcosine ethylamide in a yield of 50% (recrystallised from ethyl acetate); melting point 120°–122° C.

Analysis for $C_{16}H_{23}O_4N_3$ (321.38) Calculated: C: 59.80; H: 7.21; N: 13.08. Found: C: 59.60; H: 7.11; N: 13.28.

(ii) L-Alanyl-sarcosine ethylamide hydrobromide

In a similar manner to that described in Example 1(B) (ii), from N-benzyloxycarbonyl-L-alanyl-sarcosine ethylamide there was obtained L-alanyl-sarcosine ethylamide hydrobromide.

(iii) N-Propionyl-L-alanyl-sarcosine ethylamide

In a similar manner to that described in Example 1(B) (iii) from L-alanyl-sarcosine ethylamide hydrobromide there was obtained N-propionyl-L-alanyl-sarcosine ethylamide in a yield of 40% (chromatographed on silica gel, eluted with 2% methanol in chloroform followed by recrystallisation from ethyl acetate/petrol); melting point 149°–151° C.; $[\alpha]_D^{20} = -22.9°$ (c=1.01% in methanol).

Analysis for $C_{11}H_{21}O_3N_3$ (243.31) Calculated: C: 54.30; H: 8.70; N: 17.27. Found: C: 54.31; H: 8.88; N: 17.56.

EXAMPLE 4

(A) The Preparation of the Starting Material

(i) N-Benzyloxycarbonyl-N-methyl-L-alanine ethylamide

In a similar manner to that described in Example 1(A) (i) there was obtained N-benzyloxycarbonyl-N-methyl-L-alanine ethylamide in the form of an oil and in a yield of 86%.

(ii) N-Methyl-L-alanine ethylamide hydrobromide

In a similar manner to that described in Example 1(A) (ii), from N-benzyloxycarbonyl-N-methyl-L-alanine ethylamide there was obtained N-methyl-L-alanine ethylamide hydrobromide.

(B) The Process

(i) N-Benzyloxycarbonyl-L-alanyl-N-methyl-L-alanine ethylamide

In a similar manner to that described in Example 1(B) (i), from N-benzloxycarbonyl-L-alanine and N-methyl-L-alanine ethylamide hydrobromide there was obtained N-benzyloxycarbonyl-L-alanyl-N-methyl-L-alanine ethylamide in a yield of 25% (recrystallised from ethyl acetate/petrol); melting point 107°–110° C.

(ii) L-Alanyl-N-methyl-L-alanine ethylamide hydrobromide

In a similar manner to that described in Example 1(B) (ii), from N-benzyloxycarbonyl-L-alanyl-N-methyl-L-alanine ethylamide there was obtained L-alanyl-N-methyl-L-alanine ethylamide hydrobromide.

(iii) N-Propionyl-L-alanyl-N-methyl-L-alanine ethylamide

In a similar manner to that described in Example 1(B) (iii) from L-alanyl-N-methyl-L-alanine ethylamide hydrobromide there was obtained N-propionyl-L-alanyl-N-methyl-L-alanine ethylamide in a yield of 54% (recrystallised from ethyl acetate/petrol); melting point 124°–126° C.; $[\alpha]_D^{20} = -122.6°$ (c=1.02% in methanol).

Analysis for $C_{12}H_{23}O_3N_3$ (257.34) Calculated: C: 56.01; H: 9.01; N: 16.33. Found: C: 55.86; H: 9.08; N: 16.04.

EXAMPLE 5

(A) The Preparation of the Starting Material
N-Benzyloxycarbonyl-L-alanyl-L-proline 289 g (0.903 mol) of N-benzyloxycarbonyl-L-alanine N-hydroxysuccinimide ester were dissolved in 1800 ml of 1,2-dimethoxyethane and to this solution was added a solution of 103.98 g (0.903 mol) of L-proline in 1350 ml of water followed by 267 ml (1.8 mol) of triethylamine. The mixture was stirred for 16 hours at room temperature and then the dimethoxyethane was removed by evaporation. The aqueous solution was then extracted twice with 300 ml of ethyl acetate each time and the organic layers were discarded. The remaining solution was acidified to pH 1-2 using concentrated hydrochloric acid and extracted twice with 900 ml of ethyl acetate each time. The organic layers were combined and washed twice with 400 ml of water each time, then dried over sodium sulphate, filtered and evaporated to an oil. On trituration with 1600 ml of ether, the product crystallised out and was filtered off, washed with ether and dried to yield 193.8 g of N-benzyloxycarbonyl-L-alanyl-L-proline of melting point 124°-125° C. A second crop of 27.6 g (melting point 123°-124° C.) was obtained by evaporation of the mother liquors, trituration with 300 ml of ether and storage at 4° C. for 1 hour; total yield 77%; $[\alpha]_D^{20} = -91.2°$ (c=1.03% in methanol).

Analysis for $C_{16}H_{20}O_5N_2$ (320.35) Calculated: C: 60.00; H: 6.29; N: 8.74. Found: C: 59.91; H: 6.40; N: 8.85.

(B) The Process

(i) N-Benzyloxycarbonyl-L-alanyl-L-proline ethylamide 32 g (0.1 mol) of N-benzyloxycarbonyl-L-alanyl-L-proline were dissolved in 250 ml of dry tetrahydrofuran and the solution was cooled to −10° C. 12.7 ml (0.1 mol) of N-ethylmorpholine and 13.1 ml (0.1 mol) of isobutyl chloroformate were then added and the solution was stirred at −10° C. for 20 minutes. To this mixture was then added a further 12.7 ml of N-ethylmorpholine followed by a solution of 8.15 g (0.1 mol) of ethylammonium chloride in 50 ml of dimethylformamide. The solution was stirred for 1 hour at 0° C. then left for 16 hours at room temperature. The solvents were removed by evaporation and the residue was triturated with 450 ml of ethyl acetate and washed successively with 200 ml of 1-N hydrochloric acid, 200 ml of water and 200 ml of 5% sodium bicarbonate solution. After drying over sodium sulphate and filtration, the solvent was removed by evaporation. The resulting oil crystallised slowly from ethyl acetate ether to yield 20.7 g of N-benzyloxycarbonyl-L-alanyl-L-proline ethylamide of melting point 110°-113° C. Evaporation of the mother liquors followed by treatment with ethyl acetate/ether gave a further crop of 1.2 g of melting point 107°-110° C.; total yield 68% $[\alpha]_D^{20} = -96.0°$ (c=1.04% in methanol).

Analysis for $C_{18}H_{25}O_4N_3$ (347.42) Calculated: C: 62.24; H: 7.25; N: 12.09. Found: C: 62.16; H: 7.40; N: 11.92.

(ii) L-Alanyl-L-proline ethylamide hydrobromide 1.81 g (0.0052 mol) of N-benzyloxycarbonyl-L-alanyl-L-proline ethylamide were stirred for 1 hour in 10 ml of 4-N hydrobromic acid in acetic acid. To the solution were added 150 ml of dry ether and, after stirring for a few minutes, the oil was allowed to settle. The mixture was cooled to −60° C. and the ether decanted from the oil and discarded. The oil was then dissolved in methanol, the product crystallising out on the addition of ethyl acetate. There were obtained 1.25 g (82%) of L-alanyl-L-proline ethylamide hydrobromide of melting point 202°-204° C.

(iii) N-Pivaloyl-L-alanyl-L-proline ethylamide 1 g (0.0033 mol) of L-alanyl-L-proline ethylamide hydrobromide was dissolved in 20 ml of dry pyridine and 0.45 ml of pivaloyl chloride was added. The mixture was stirred for 1 hour at room temperature and then the pyridine was removed by evaporation. The oil was triturated with toluene, re-evaporated and then partitioned between chloroform and saturated brine. The chloroform layer was separated and dried over magnesium sulphate, filtered off and evaporated to a clear oil which crystallised on the addition of petrol. The solid was filtered off, washed with petrol and dried to yield 0.4 g (40%) of N-pivaloyl-L-alanyl-L-proline ethylamide of melting point 94°-96° C.

Microanalysis showed the product to contain 0.6 mol of chloroform even after intensive drying. It was therefore dissolved in water and freeze-dried to give the monohydrate; $[\alpha]_D^{20} = -109.7°$ (c=0.95% in methanol).

Analysis for $C_{15}H_{27}N_3O_3$ (297.4) Calculated: C: 60.58; H: 9.15; N: 14.13. Found: C: 57.55; H: 9.11; N: 13.24; $H_2O$: 5.01%.

Water-free: C: 60.59; H: 9.01; N: 13.94.

(iv) N-Benzoyl-L-alanyl-L-proline ethylamide 1.42 g (0.0048 mol) of L-alanyl-L-proline ethylamide hydrobromide were dissolved in 20 ml of methylene chloride, 21.8 ml (0.01 mol) of 0.5-N sodium hydroxide solution were added followed by 0.54 ml (0.0053 mol) of benzoyl chloride. The mixture was stirred vigorously at room temperature for 1 hour with care being taken that the solution remained basic, this being achieved by the addition of a few drops of 0.5-N sodium hydroxide solution. The layers were then allowed to separate and the methylene chloride layer was separated, dried over magnesium sulphate and evaporated to an oil which crystallised on treatment with ethyl acetate. The crystals were filtered off, washed and dried to yield 1.05 g of N-benzoyl-L-alanyl-L-proline ethylamide of melting point 200°-202° C.; $[\alpha]_D^{20} = -82.7°$ (c=0.99 in methanol).

Analysis for $C_{17}H_{23}O_3N_3$ (317.39) Calculated: C: 64.33; H: 7.30; N: 13.24. Found: C: 64.17; H: 7.44; N: 12.98.

(v) N-(n-Valeryl)-L-alanyl-L-proline ethylamide 1.0 g (0.0033 mol) of L-alanyl-L-proline ethylamide hydrobromide was dissolved in 20 ml of dry pyridine and 1.14 ml (0.0066 mol) of n-valeric anhydride were added. The mixture was stirred for 1 hour at room temperature and then the pyridine was removed by evaporation. The oily residue was dissolved in 80 ml of water and extracted twice with 50 ml of chloroform each time. The organic layers were combined, washed with 5% citric acid solution, water and 5% sodium bicarbonate solution, dried over magnesium sulphate and evaporated. The residue was crystallised from chloroform/petrol to yield 0.5 g (51%) of N-(n-valeryl)-L- alanyl-L-proline ethylamide of melting point 110°–111° C.; $[\alpha]_D^{20} = -123.2°$ (c=1.15% in methanol).

Analysis for $C_{15}H_{27}O_3N_3$ (297.4) Calculated: C: 60.58; H: 9.15; N: 14.13. Found: C: 60.52; H: 9.16; N: 13.97.

(vi) N-Ethoxycarbonyl-L-alanyl-L-proline ethylamide 2 g (0.0066 mol) of L-alanyl-L-proline ethylamide hydrobromide were suspended in 20 ml of dry tetrahydrofuran, 1.84 ml (0.0145 mol) of N-ethylmorpholine and 0.76 ml (0.0079 mol) of ethyl chloroformate were added and the mixture was stirred at room temperature for 2 hours. The solvent was evaporated off and the residue dissolved in 100 ml of chloroform and washed successively with 2-N hydrochloric acid in brine, brine, saturated sodium bicarbonate solution and brine, dried over magnesium sulphate and evaporated to an oil which soon crystallised. Recrystallisation from chloroform/petrol yielded 0.88 g (47%) of N-ethoxycarbonyl-L-alanyl-L-proline ethylamide of melting point 126°–128° C.; $[\alpha]_D^{20} = -117.6°$ (c=1.02% in methanol).

Analysis for $C_{13}H_{23}O_4N_3$ (285.35) Calculated: C: 54.73; H: 8.12; N: 14.72. Found: C: 54.63; H: 8.04; N: 14.53.

(vii) N-Propionyl-L-alanyl-L-proline ethylamide

From L-alanyl-L-proline ethylamide hydrobromide and propionic anhydride there was obtained according to the procedure described in part (v) of this Example N-propionyl-L-alanyl-L-proline ethylamide in a yield of 66% (recrystallised from ethyl acetate); melting point 173°–175° C.; $[\alpha]_D^{20} = -63.9°$ (c=0.99% in water).

Analysis for $C_{13}H_{23}O_3N_3$ (269.35) Calculated: C: 57.98; H: 8.61; N: 15.60. Found: C: 58.16; H: 8.80; N: 15.88.

(viii) N-Phenacetyl-L-alanyl-L-proline ethylamide

From L-alanyl-L-proline ethylamide hydrobromide and phenacetyl chloride there was obtained according to the procedure described in part (iv) of this Example N-phenacetyl-L-alanyl-L-proline ethylamide in a yield of 50% (recrystallised from ethyl acetate/petrol); melting point 127°–130° C.; $[\alpha]_D^{20} = -132.6°$ (c=0.94% in methanol).

Analysis for $C_{18}H_{25}O_3N_3$ (331.42) Calculated: C: 65.24; H: 7.60; N: 12.68. Found: C: 65.25; H: 7.61; N: 12.76.

(ix) N-Isobutanoyl-L-alanyl-L-proline ethylamide

From L-alanyl-L-proline ethylamide hydrobromide and isobutyric anhydride there was obtained according to the procedure described in part (v) of this Example N-isobutanoyl-L-alanyl-L-proline ethylamide in a yield of 54% (recrystallised from ethyl acetate/petrol); melting point 155°–157° C.; $[\alpha]_D^{20} = -132.1°$ (c=1.02% in methanol).

Analysis for $C_{14}H_{25}O_3N_3$ (283.37) Calculated: C: 59.34; H: 8.89; N: 14.83. Found: C: 59.31; H: 8.91; N: 15.00.

(x) N-Cyclohexylcarbonyl-L-alanyl-L-proline ethylamide 1.25 g (0.00425 mol) of L-alanyl-L-proline ethylamide hydrobromide were suspended in 20 ml of dichloromethane and to the suspension were added 17.84 ml (0.00892 mol) of 0.5-N sodium hydroxide solution followed by 0.62 ml (1.1 equivalents) of cyclohexane carboxylic acid chloride. The mixture was stirred vigorously for 1 hour. The solution was diluted with 80 ml of dichloromethane, the organic layer was separated, washed with 60 ml of brine, dried over magnesium sulphate and evaporated to give a solid. Recrystallisation from ethyl acetate yielded 0.83 g (60%) of N-cyclohexylcarbonyl-L-alanyl-L-proline ethylamide of melting point 190.5°–191.5° C.; $[\alpha]_D^{20} = -116.0°$ (c=1.055% in methanol).

Analysis for $C_{17}H_{29}O_3N_3$ (323.44) Calculated: C: 63.13; H: 9.04; N: 12.99. Found: C: 63.24; H: 8.94; N: 12.92.

(xi) N-(p-Toluenesulphonyl)-L-alanyl-L-proline ethylamide 1.0 g (0.0033 mol) of L-alanyl-L-proline ethylamide hydrobromide was dissolved in 20 ml of dry pyridine and 0.63 g (0.0033 mol) of p-toluenesulphonyl chloride was added. The mixture was stirred at room temperature for 1 hour and the pyridine was then removed by evaporation. The oily residue was dissolved in chloroform and the solution was washed with water, dried over magnesium sulphate and evaporated to an oil. This oil was dissolved in water and freeze-dried to yield 0.40 g (33%) of N-(p-toluenesulphonyl)-L-alanyl-L-proline ethylamide; $[\alpha]_D^{20} = -90.7°$ (c=0.94% in water).

Analysis for $C_{17}H_{25}O_4N_3S$ (367.47) Calculated: C: 55.57; H: 6.86; N: 11.42. Found: C: 54.06; H: 7.01; N: 11.13; $H_2O$: 2.41.

Water-free: C: 55.36; H: 6.91; N: 11.40.

(xii) N-(1-Adamantylcarbonyl)-L-alanyl-L-proline ethylamide 2.93 g (0.010 mol) of L-alanyl-L-proline ethylamide hydrobromide were dissolved in 50 ml of tetrahydrofuran and the mixture was cooled to 0° C. There were then added 2.8 ml (0.020 mol) of triethylamine followed by 2.15 g (0.010 mol) of 1-adamantoyl chloride. The mixture was stirred at 0° C. for 0.5 hour and at room temperature for 2 hours and then evaporated to dryness. The oily residue was dissolved in ethyl acetate and the solution washed successively with 0.5-N hydrochloric acid, water, 5% sodium bicarbonate solution and water, dried over sodium sulphate and evaporated. The resulting oil was crystallised from ethyl acetate/petroleum ether to yield 2.2 g (59%) of N-(1-adamantylcarbonyl)-L-alanyl-L-proline ethylamide of melting point 116°–118° C; $[\alpha]_D^{20} = -88.1°$ (c=0.99% in methanol).

Analysis for $C_{21}H_{33}O_3N_3$ (375.5) Calculated: C: 67.17; H: 8.86; N: 11.19. Found: C: 67.22; H: 8.92; N: 11.35.

(xiii) N-(D-10-Camphorsulphonyl)-L-alanyl-L-proline ethylamide 2.93 g (0.010 mol) of L-alanyl-L-proline ethylamide hydrobromide were dissolved in 30 ml of methylene chloride and there were then added 40 ml of 0.5-N sodium hydroxide solution followed by 2.5 g (0.010 mol) of D-10-camphorsulphonyl chloride. The mixture was stirred vigorously at room temperature for 3 hours. The organic layer was then separated, washed successively with water, 0.5-N hydrochloric acid and water, dried over magnesium sulphate and evaporated to an oil. This oil was chromatographed on 100 g of silica gel using chloroform for the elution. Evaporation of the chloroform eluate in a high vacuum yielded 1.8 g (42%) of N-(D-10-camphorsulphonyl)-L-alanyl-L-proline ethylamide in the form of a hygroscopic foam; $[\alpha]_D^{20} = -52.9°$ (c=0.99% in methanol).

Analysis for $C_{20}H_{33}O_5N_3S$ (427.6) Calculated: C: 56.18; H: 7.78; N: 9.83. Found: C: 55.52; H: 7.66; N: 9.58; $H_2O$: 1.10.

Water-free: C: 56.14; H: 7.62; N: 9.69.

EXAMPLE 6

(A) The preparation of the starting material

N-Benzyloxycarbonyl-L-alanyl-L-proline

This compound was prepared as described in Example 5(A).

(B) The process (i) N-Benzyloxycarbonyl-L-alanyl-L-proline methylamide

In a similar manner to that described in Example 5(B) (i) there was prepared N-benzyloxycarbonyl-L-alanyl-L-proline methylamide in a yield of 64% (recrystallised from ethyl acetate/ether); melting point 126°–129° C; $[\alpha]_D^{20} = -95.6°$ (c = 1.01% in methanol).

Analysis for $C_{17}H_{23}O_4N_3$ (333.39) Calculated: C: 61.24; H: 6.95; N: 12.60. Found: C: 61.21; H: 7.08; N: 12.68.

(ii) N-Propionyl-L-alanyl-L-proline methylamide 2.5 g (0.0075 mol) of N-benzyloxycarbonyl-L-alanyl-L-proline methylamide were dissolved in 4-N hydrobromic acid in acetic acid (15 ml) and stirred for 1 hour at room temperature. 200 ml of dry ether were added and the solid was allowed to settle. The ether solution was decanted off and the hygroscopic solid washed with ether and dried under a vacuum.

The solid was dissolved in 50 ml of dry pyridine, 1.95 ml of propionic anhydride were added and the mixture was stirred for 2 hours at room temperature. The solvent was removed by evaporation and the residue extracted with 80 ml of chloroform. The organic layer was washed with 50 ml of brine and evaporated to an oil which crystallised on the addition of ethyl acetate. The crude product was chromatographed on 100 g of silica gel and eluted with 2% methanol in chloroform. The pure material was crystallised from ethyl acetate to yield 0.5 g of N-propionyl-L-alanyl-L-proline methylamide of melting point 163°–165° C.; $[\alpha]_D^{20} = -137.0°$ (c = 1.02% in methanol).

Analysis for $C_{12}H_{21}O_3N_3$ (255.32) Calculated: C: 56.45; H: 8.29; N: 16.46. Found: C: 56.31; H: 8.02; N: 16.52.

EXAMPLE 7

(A) The preparation of the starting material

N-Benzyloxycarbonyl-L-alanyl-L-proline

This compound was prepared as described in Example 5(A).

(B) The process (i) N-Benzyloxycarbonyl-L-alanyl-L-proline isopropylamide

In a similar manner to that described in part (B) (i) of this Example there was prepared N-benzyloxycarbonyl-L-alanyl-L-proline isopropylamide in a yield of 44% (recrystallised from ethyl acetate/petrol); melting point 124°–126° C.

(ii) N-Propionyl-L-alanyl-L-proline isopropylamide

In a similar manner to that described in Example 6(B) (ii) there was prepared N-propionyl-L-alanyl-L-proline isopropylamide in a yield of 61% (recrystallised from ethyl acetate/petrol); melting point 173°–175° C.; $[\alpha]_D^{20} = -127.2°$ (c = 0.93% in methanol).

Analysis for $C_{14}H_{25}O_3N_3$ (283.37) Calculated: C: 59.34; H: 8.89; N: 14.83. Found: C: 59.34; H: 8.72; N: 14.88.

The following Example illustrates pharmaceutical preparations containing the dipeptide derivatives provided by the present invention:

EXAMPLE A

An aerosol composition can contain the following ingredients:

| Ingredient | Percent by weight |
|---|---|
| Dipeptide derivative | 1–5 |
| Ethanol | 15–35 |
| Propellant* | ad 100 |

*The propellant can be dichlorodifluoromethane or a 5:1 mixture of dichlorotetrafluoroethane and dichlorotetrafluoromethane.

What is claimed:

1. Dipeptide derivatives of the formula $$R^3-NH-\underset{(L)}{CH}(CH_3)-CO-N(R^2)-\underset{*}{CH}(R^1)-CO-NH-R \quad (I)$$

wherein R is methyl, ethyl, propyl or isopropyl; $R^1$ and $R^2$ each is hydrogen or methyl, with the proviso that $R^1$ and $R^2$ are not simultaneously hydrogen or $R^1$ and $R^2$ together are trimethylene; $R^3$ is selected from unsubstituted alkanoyl containing at least 3 carbon atoms or halo-alkanoyl, nitro-alkanoyl, cyano-alkanoyl, cycloalkylcarbonyl, cyclo-alkyl-alkanoyl, aroyl, arylalkanoyl, alkoxycarbonyl, aryloxycarbonyl, arylsulphonyl, alkylsulphonyl, cycloalkylsulphonyl, cyclo alkylsulphinyl, cyclo-alkyl-alkylsulphonyl or cycloalkyl-alkylsulphinyl and the asterisk denotes the configuration at the carbon atom so-marked is L when $R^1$ is other than hydrogen.

2. Dipeptide derivatives of claim 1, wherein $R^1$ is hydrogen and $R^2$ is methyl or $R^1$ and $R^2$ together are trimethylene.

3. Dipeptide derivatives of claim 1, wherein $R^3$ is aroyl.

4. Dipeptide derivatives of claim 3, wherein $R^3$ is benzoyl.

5. Dipeptide derivatives of claim 1 wherein R is ethyl.

6. The compound of claim 1 which is: N-propionyl-L-alanyl-L-proline methylamide.

7. The compound of claim 1 which is: N-pivaloyl-L-alanyl-L-proline ethylamide.

8. The compound of claim 1 which is: N-benzoyl-L-alanyl-L-proline ethylamide.

9. The compound of claim 1 which is: N-(n-valeryl)-L-alanyl-L-proline ethylamide.

10. The compound of claim 1 which is: N-ethoxycarbonyl-L-alanyl-L-proline ethylamide.

11. The compound of claim 1 which is: N-propionyl-L-alanyl-L-proline ethylamide.

12. The compound of claim 1 which is: N-phenacetyl-L-alanyl-L-proline ethylamide.

13. The compound of claim 1 which is: N-isobutanoyl-L-alanyl-L-proline ethylamide.

14. The compound of claim 1 which is: N-cyclohexylcarbonyl-L-alanyl-L-proline ethylamide.

15. The compound of claim 1 which is: N-(p-toluenesulphonyl)-L-alanyl-L-proline ethylamide.

16. The compound of claim 1 which is: N-(1-adamantylcarbonyl)-L-alanyl-L-proline ethylamide.

17. The compound of claim 1 which is: N-(D-10-camphorsulphonyl)-L-alanyl-L-proline ethylamide.

18. The compound of claim 1 which is: N-propionyl-L-alanyl-L-proline isopropylamide.

19. The compound of claim 1 which is: N-propionyl-L-alanyl-alanine ethylamide.

20. The compound of claim 1 which is: N-benzoyl-L-alanyl-L-alanine ethylamide.

21. The compound of claim 1 which is: N-pivaloyl-L-alanyl-L-alanine ethylamide.

22. The compound of claim 1 which is: N-propionyl-L-alanyl-L-alanine isopropylamide.

23. The compound of claim 1 which is: N-propionyl-L-alanyl-N-methyl-L-alanine ethylamide.

24. The compound of claim 1 which is: N-propionyl-L-alanyl-sarcosine ethylamide.

* * * * *